(12) United States Patent
Catani et al.

(10) Patent No.: US 7,049,435 B2
(45) Date of Patent: May 23, 2006

(54) EXTRACTIVE METHODS FOR PURIFYING SUCRALOSE

(75) Inventors: Steven J. Catani, Athens, GA (US); Nicholas M. Vernon, Daphne, AL (US); David Saul Neiditch, Athens, GA (US); James Edwin Wiley, Jr., Daphne, AL (US); Edward Micinski, Martinez, GA (US)

(73) Assignee: Tate & Lyle Public Limited Company, London (GB)

(*) Notice: Subject to any disclaimer, the term of this patent is extended or adjusted under 35 U.S.C. 154(b) by 406 days.

(21) Appl. No.: 10/092,715

(22) Filed: Mar. 8, 2002

(65) Prior Publication Data

US 2003/0171574 A1    Sep. 11, 2003

(51) Int. Cl.
*C07H 1/06*    (2006.01)
(52) U.S. Cl. .................. 536/124; 536/1.11; 536/127
(58) Field of Classification Search .............. 536/1.11, 536/123.12, 127, 124
See application file for complete search history.

(56) References Cited

U.S. PATENT DOCUMENTS

| | | | |
|---|---|---|---|
| 4,343,934 A | 8/1982 | Jenner et al. | 536/122 |
| 4,362,869 A | 12/1982 | Jenner et al. | 536/122 |
| 4,380,476 A | 4/1983 | Mufti et al. | 127/46.3 |
| 4,405,654 A | 9/1983 | Lee | 426/658 |
| 4,826,962 A | 5/1989 | Rathbone et al. | 536/122 |
| 4,980,463 A | 12/1990 | Walkup et al. | 536/124 |
| 5,034,551 A | 7/1991 | Vernon et al. | 556/89 |
| 5,128,248 A | 7/1992 | Dordick et al. | 435/100 |
| 5,141,860 A | 8/1992 | Bornemann et al. | 435/100 |
| 5,270,071 A | 12/1993 | Sharp et al. | 426/577 |
| 5,272,137 A | 12/1993 | Blasé et al. | 514/54 |
| 5,298,611 A | 3/1994 | Navia et al. | 536/4.1 |
| 5,354,902 A | 10/1994 | Merciadez et al. | 562/601 |
| 5,374,659 A | 12/1994 | Gowan, Jr. | 514/557 |
| 5,384,311 A * | 1/1995 | Antenucci et al. | 514/53 |
| 5,397,588 A | 3/1995 | Antenucci et al. | 426/573 |
| 5,409,907 A | 4/1995 | Blase et al. | 514/54 |
| 5,498,709 A * | 3/1996 | Navia et al. | 536/124 |
| 5,530,106 A | 6/1996 | Navia et al. | 536/4.1 |
| 5,593,696 A | 1/1997 | McNally et al. | 424/472 |
| 5,621,005 A | 4/1997 | Gowan, Jr. | 514/557 |
| 5,658,919 A | 8/1997 | Ratnaraj et al. | 514/269 |
| 5,674,522 A | 10/1997 | Shah et al. | 424/439 |
| 5,817,340 A | 10/1998 | Roche et al. | 424/470 |
| 5,876,759 A | 3/1999 | Gowan, Jr. | 424/494 |
| 5,977,349 A | 11/1999 | Catani et al. | 536/124 |
| 6,080,481 A | 6/2000 | Ochs et al. | 428/372 |
| 6,090,401 A | 7/2000 | Gowan, Jr. et al. | 424/439 |
| 6,211,246 B1 | 4/2001 | Gelotte et al. | 514/653 |
| 6,258,381 B1 | 7/2001 | Luber et al. | 424/464 |
| 6,277,409 B1 | 8/2001 | Luber et al. | 424/476 |

FOREIGN PATENT DOCUMENTS

WO    WO 00/01253    1/2000

OTHER PUBLICATIONS

Burke, J. AIC Book and Paper Group Annual, vol. 3, 1984, 13-58.*
Shamil et al., 25 Lebensm. Wiss. U. Technol. 192-96 (1992).
Burke, 3 AIC Book and Paper Group International 13 (1984), at http://palimpsest.stanford.edu/byauth/burke/solpar.

* cited by examiner

*Primary Examiner*—James O. Wilson
*Assistant Examiner*—Ganapathy Krishnan
(74) *Attorney, Agent, or Firm*—RatnerPrestia (57) ABSTRACT

The present invention relates to novel extractive methods for purifying sucralose. The present invention also relates to compositions comprising the sucralose preparations made by the methods of the present invention.

38 Claims, 2 Drawing Sheets

Figure 1

Figure 2

EXTRACTIVE METHODS FOR PURIFYING SUCRALOSE

FIELD OF THE INVENTION

The present invention relates to novel extractive methods for purifying sucralose. The present invention also relates to compositions comprising the sucralose preparations made by the methods of the present invention.

BACKGROUND OF THE INVENTION

Sucralose, 4,1',6'-trichloro-4,1',6'-trideoxygalactosucrose, a sweetener with a sweetness intensity several hundred times that of sucrose, is derived from sucrose by replacing the hydroxyl groups in the 4, 1', and 6' positions with chlorine. Synthesis of sucralose is technically challenging because of the need to selectively replace specific hydroxyl groups with chlorine atoms, while preserving other hydroxyl groups including a highly reactive primary hydroxyl group. Numerous approaches to this synthesis have been developed. See, e.g., U.S. Pat. Nos. 4,362,869; 4,826,962; 4,980,463; and 5,141,860, which are expressly incorporated by reference herein. However, such approaches typically provide a product that contains varying levels of other chlorinated sugar compounds in addition to sucralose. Although much effort has been directed toward the synthesis of sucralose, the isolation of sucralose in highly pure form from this complex mixture of contaminants heretofore has received relatively little attention. Early reported work typically involved crystallizing sucralose directly from the synthesis mixture, a process that yields a material with high impurity levels. Sucralose is sometimes purified from a synthesis mixture by silica gel chromatography. See, e.g., U.S. Pat. No. 5,128,248, which is expressly incorporated by reference herein. That procedure, due to its use of silica gel, may be ill-suited to large-volume commercial production of highly pure sucralose. In addition, relatively little attention has been focused on other approaches for removing halogenated sugar impurities from sucralose. Efficient removal of these impurities is important because, even at quite low concentrations, they can have an adverse impact on the sweetness, taste, and flavor-modifying properties of sucralose.

Various methods for the synthesis of sucralose and related compounds have been suggested. U.S. Pat. No. 4,405,654, which is expressly incorporated by reference herein, for example, relates to a process for the synthesis of a related compound, 1',4',6'-trichloro-1',4',6'-trideoxysucrose. After the deacetylation of a pentaacetate precursor, the reaction mixture is purified by column chromatography on silica gel. The product is eluted from the silica gel with ethyl acetate.

U.S. Pat. No. 4,980,463, which is expressly incorporated by reference herein, relates to a process in which sucralose is produced by KOH treatment of a methanol solution of sucralose-6-benzoate. The methanol is removed by evaporation, and the residue is dissolved in water. The aqueous solution is extracted three times with separate one-quarter volumes of ethyl acetate. The combined organic extracts are concentrated and then back extracted with water to recover sucralose present in the ethyl acetate. The combined aqueous portions are concentrated and treated with a decolorizing agent. Additional concentration permits crystallization of the sucralose. The recovered crystals have a reported purity of 99.6%. Purification to this level is achieved primarily through crystallization, rather than by solvent extraction processes. It is noteworthy that this approach only involves ethyl acetate extraction of the original aqueous solution, and sucralose is never re-extracted from the aqueous solution into an organic phase, thereby achieving a further purification.

U.S. Pat. No. 5,034,551, which is expressly incorporated by reference herein, relates to a similar process in which a base is used to hydrolyze a solution of sucralose-6-benzoate in methanol. The methanol is removed by evaporation, and the sucralose-containing residue is dissolved in water. This solution is extracted three times with separate one-quarter volumes of ethyl acetate. The remaining aqueous layer is decolorized with charcoal, concentrated, and the sucralose is allowed to crystallize.

U.S. Pat. No. 5,498,709, which is expressly incorporated by reference herein, relates to solvents that may be used to extract sucralose from the aqueous brine produced by alkaline hydrolysis of a 6-acyl ester precursor compound. Possible solvents include methyl acetate, ethyl acetate, methyl ethyl ketone, methyl isobutyl ketone, methyl isoamyl ketone, methylene chloride, chloroform, diethyl ether, and methyl tertiary butyl ether. Ethyl acetate is presented as a suitable solvent for reasons of extraction selectivity, ease of recycling, and toxicological safety.

U.S. Pat. No. 5,498,709, which is expressly incorporated by reference herein, also relates to a process in which the aqueous solution remaining after ester hydrolysis of sucralose precursors is concentrated and then sucralose is isolated by three sequential extractions with ethyl acetate or other suitable solvent. The extracts may then be combined, and optionally washed with water to remove any dimethylformamide remaining prior to recovering the sucralose by concentration and crystallization. This patent also relates to processes in which sucralose contained in the aqueous brine obtained after alkaline deesterification is extracted into a solvent not miscible in brine, such as dichloromethane, chloroform, 2-butanone, cyclohexanone, or ethyl acetate. The organic extracts may then be back extracted with water to transfer the sucralose back into the aqueous phase. This aqueous solution may then be decolorized, concentrated, and the resulting purified sucralose is recovered by crystallization. This approach yields a relatively impure material.

An additional approach discussed within U.S. Pat. No. 5,498,709, which is expressly incorporated by reference herein, involves the toluene extraction of the alkaline solution remaining after deesterification. Specifically, the solution is extracted twice with toluene to remove non-polar impurities. The aqueous solution is then extracted repeatedly with 2-butanone. The 2-butanone extracts are combined, and the solvent is evaporated to yield a reddish syrup containing sucralose.

U.S. Pat. No. 5,530,106, which is expressly incorporated by reference herein, relates to an extractive process for a crude sucralose solution obtained after alkaline hydrolysis of sucralose-6-acetate and subsequent neutralization. The aqueous sucralose solution is extracted with water saturated ethyl acetate. Some impurities are selectively partitioned to the organic phase by this extraction. Subsequently, the ethyl acetate phase is backwashed with water in order to recover a portion of the sucralose that had also partitioned into the organic phase. The aqueous solution and the aqueous backwash are combined, concentrated, decolorized, and the sucralose is recovered by crystallization from the aqueous phase.

Extant methods involving crystallization without the use of at least two carefully controlled solvent extractions fail to effectively remove impurities both more polar and less polar than sucralose. Hence, a less expensive and more effective method is needed for the commercial production of sucralose. The present inventions attempt to solve these problems and provide methodologies that are both commercially practicable and effective at removing impurities.

SUMMARY OF THE INVENTION

One embodiment of the invention relates to methods for removing impurities from a composition comprising sucralose and impurities in a first solvent comprising the steps of performing a liquid extraction of the composition with a second at least partially immiscible solvent to effect removal of the impurities into the second solvent and performing a second extraction of the composition with a third at least partially immiscible solvent to effect the transfer of the sucralose into the third solvent and the retention of the impurities in the first solvent.

Another embodiment of the present invention relates to methods for removing impurities from a composition comprising an aqueous solution of sucralose and impurities comprising the steps of performing a liquid extraction of the composition with an at least partially immiscible non-aromatic organic solvent to effect removal of the impurities into the solvent and performing a second extraction of the composition with an organic solvent to effect the transfer of the sucralose into the solvent and the retention of the impurities in the aqueous phase.

The invention herein also relates to methods for removing impurities from a composition comprising an aqueous solution of sucralose and impurities comprising the steps of performing a liquid extraction of the composition with an at least partially immiscible organic solvent to effect the transfer of the impurities into the solvent, performing a second extraction of the composition with an organic solvent to effect the transfer of the sucralose into the solvent and the retention of the impurities in the aqueous phase, extracting the organic solvent remaining from the first step with an aqueous solution to effect the transfer of the sucralose present in the organic phase into the aqueous solution and combining the aqueous solution so obtained in the third step with the aqueous solution recovered in the first step prior to performing the second step.

Another embodiment of the present invention relates to methods for removing tetrachlorosucrose compounds from a solution of sucralose and halogenated sucrose derivatives in a first solvent comprising extracting the solution of sucralose and other halogenated sucralose derivatives with an at least partially immiscible non-aromatic second solvent to effect the partition of the tetrachlorosucrose compounds into the second solvent and the retention of the sucralose in the first solvent.

An additional embodiment of the present invention relates to methods for removing impurities from a composition comprising a solution of sucralose and impurities in a first solvent comprising the steps of performing a liquid extraction of the composition with a second solvent that possesses a lower Hildebrand parameter than the first solvent under conditions that selectively transfer impurities less polar than sucralose into the second solvent thereby providing a sucralose solution in the first solvent that has an increased ratio of sucralose to impurities less polar than sucralose and performing a liquid extraction of the composition with a third solvent that possesses a higher Hildebrand parameter than the first solvent under conditions that selectively transfer impurities more polar than sucralose into the third solvent thereby providing a sucralose solution in the first solvent with an increased ratio of sucralose to impurities more polar than sucralose.

Also contemplated within the scope of the present invention are methods for removing impurities from a composition comprising a solution of sucralose and impurities in a first solvent comprising the steps of performing a liquid extraction of the composition with a second solvent that possesses a higher Hildebrand parameter than the first solvent under conditions that selectively transfer sucralose into the second solvent thereby providing a sucralose solution in the second solvent that has an increased ratio of sucralose to impurities less polar than sucralose and performing a liquid extraction of the sucralose solution in the second solvent obtained in the previous step with a third solvent that possesses a higher Hildebrand parameter than the second solvent under conditions that selectively transfer impurities more polar than sucralose into the third solvent thereby providing a sucralose solution in the second solvent that has an increased ratio of sucralose to impurities more polar than sucralose.

Also contemplated within the scope of the present invention are sucralose preparations obtained by any one and/or some combination of the methodologies of the present invention as well as products comprising the sucralose preparations obtained by any one and/or some combination of the methodologies of the present invention.

Other objectives, features and advantages of the present invention will become apparent from the following detailed description. The detailed description and the specific examples, although indicating specific embodiments of the invention, are provided by way of illustration only. Accordingly, the present invention also includes those various changes and modifications within the spirit and scope of the invention that may become apparent to those skilled in the art from this detailed description.

DETAILED DESCRIPTION OF THE INVENTION

It is understood that the present invention is not limited to the particular methodologies, protocols, pH, and reagents, etc., described herein, as these may vary. It is also to be understood that the terminology used herein is used for the purpose of describing particular embodiments only, and is not intended to limit the scope of the present invention. It must be noted that as used herein and in the appended claims, the singular forms "a," "an," and "the" include plural reference unless the context clearly dictates otherwise. Thus, for example, a reference to "a solvent" is a reference to one or more solvents and includes equivalents thereof known to those skilled in the art and so forth.

Unless defined otherwise, all technical and scientific terms used herein have the same meanings as commonly understood by one of ordinary skill in the art to which this invention belongs. Preferred methods, devices, and materials are described, although any methods and materials similar or equivalent to those described herein can be used in the practice or testing of the present invention. All references cited herein are incorporated by reference herein in their entirety.

Definitions

Aromatic: as used herein includes solvents containing cyclic compounds with resonant conjugated double bond structures such as, for example, benzene, toluene, or xylene.

Backwash: as used herein includes an extractive step in which a second solvent phase remaining after its use to extract a first solvent is re-extracted with a small portion of the first solvent. This provides a means for recovering valuable materials such as sucralose that have partially partitioned into the second solvent which may be employed to semiselectively remove impurities. The backwash solution may be combined with the first solvent, so that the recovery of the valuable product such as sucralose may be maximized in the first solvent. The backwash solution optionally may be concentrated prior to its addition to the first solvent.

Beverage: as used herein includes any non-carbonated or carbonated beverage such as cola, diet cola, soda, diet soda, juice cocktail, root beer, birch beer, any fountain drink, sparkling fruit juice, water, sparkling water, tonic water, sport drink, and club soda. Beverage may also include any non-alcoholic or alcoholic drink such as any beer, including ale, pilsner, lager, or derivation thereof, malt liquor, red wine, white wine, sparkling wine, fortified wine, wine cooler, wine spritzer, any pre-made cocktail mixer including margarita mix, sour mix, or daiquiri mix, any fermented fruit or tea beverage, hard liquor, and any flavored liqueur such as brandy, schnapps, bitters, or cordial. Beverage may include any dairy, milk, or cream product or any diary, cream, or milk substitute such as half & half, non-dairy creamer, powdered creamer, flavored creamer, soy milk product, and lactose-free milk product. Beverage may also include any fruit or vegetable juice in whole, concentrated, or powdered form and any combination of fruit and vegetable juices or other beverages. Beverage may also include coffee, any coffee drink, any coffee flavoring syrup, tea, iced tea, and cocoa, as well as any combination of any of the foregoing.

Combination sweetener: as used herein includes any combination or permutation of sweeteners, including combinations of sucralose, saccharin, aspartame, acesulfame potassium, cyclamate, alitame, stevioside, glucose, fructose, levulose, maltose, lactose, any sugar alcohol, sorbitol, xylitol, and mannitol.

Consumer product: as used herein includes fruit products such as applesauce, jams, jellies, marmalades, fruit snacks, fruit butters, and fruit spreads. Consumer product may also include any dairy, milk, or cream product, such as cheese, ice cream, and yogurt. Consumer product includes baked goods such as breads, doughnuts, cakes, cheesecakes, danishes, pastries, pies, bagels, cookies, scones, crackers, muffins, and wafers. Consumer product includes cereal products such as cold cereals, grits, hot cereals, granola mixes, oatmeal, and trail mixes. Consumer product includes condiments such as butter, peanut butter, whipped cream, sour cream, BBQ sauce, chili, syrup, gravy, mayonnaise, olives, seasonings, relish, pickles, sauces, snack dips, ketchup, salsa, mustard, salad dressings, and pickled peppers. Consumer product includes snack foods such as pudding, candy bars, hard candy, chocolate products, lollipops, fruit chews, marshmallows, chewing gum, bubble gum, gummy bears, taffy, pie fillings, syrups, gel snacks, mints, popcorn, chips, and pretzels. Consumer product includes meat products such as hot dogs, canned fish, sausage, prepared meats, canned meat, dehydrated meat, and luncheon meat. Consumer product includes soups, consomme, and bullion. Consumer product includes dental products such as toothpaste, dental floss, mouthwash, denture adhesive, enamel whitener, fluoride treatments, and oral care gels. Consumer product includes cosmetic items such as lipstick, lip balm, lip gloss, and petroleum jelly. Consumer product includes therapeutic items such as non-tobacco snuff, tobacco substitutes, pharmaceutical compositions, chewable medications, cough syrups, throat sprays, throat lozenges, cough drops, antibacterial products, pill coatings, gel caplets, soluble fiber preparations, antacids, tablet cores, rapidly absorbed liquid compositions, stable foam compositions, rapidly disintegrating pharmaceutical dosage forms, beverage concentrates for medicinal purposes, aqueous pharmaceutical suspensions, liquid concentrate compositions, and stabilized sorbic acid solutions. Consumer product includes nutritional products such as meal replacement bars, meal replacement shakes, dietary supplements, protein mixes, protein bars, carbohydrate control bars, low carbohydrate bars, meal supplements, electrolyte solutions, whey protein products, metabolic response modifiers, appetite control beverages, and echinacea sprays. Consumer product includes animal foodstuffs such as dog and cat food, and bird feed. Consumer product includes foodstuffs such as baby food. Consumer product includes tobacco products such as pipe tobacco, cigarette tobacco, and chewing tobacco.

Crystallization: as used herein includes processes in which a solution is rendered saturated or supersaturated with respect to a dissolved component, and the formation of crystals of this component is achieved. The initiation of crystal formation may be spontaneous, or it may require the addition of seed crystals. As used herein, crystallization also describes the situation in which a solid or liquid material is dissolved in a solvent to yield a solution which is then rendered saturated or supersaturated so as to obtain crystals. Also, included in the term crystallization are the ancillary processes of washing the crystals with one or more solvents, drying the crystals, and harvesting the final product so obtained.

Feed mixture: as used herein includes any mixture of compounds that results from any synthetic process for sucralose. Includes mixtures of sucralose and any and all impurities.

Impurity: as used herein includes compounds other than sucralose and includes products of any number of processes for synthesizing sucralose that are not sucralose. Impurity includes any monochloro-, dichloro-, tetrachloro-, and pentachloro-derivative of sucrose and any other disaccharide derived from sucrose, as well as any trichloro-derivative other than sucralose itself, whether present in free form or as esters of carboxylic acids. Impurity includes any of the halogenated sugar derivatives within Tables 1 through 4, such as dichlorosucrose acetate, 6,1',6'-trichlorosucrose, 4,6,6'-trichlorosucrose, 4,1',4',6'-tetrachlorogalactotagatose, 4,1',6'-trichlorogalactosucrose-6-acetate, 4,6,1',6'-tetrachlorogalactosucrose, 4,1'-dichlorogalactosucrose, 3',6'-dichloroanhydrosucrose, 4,6'-dichlorogalactosucrose, 1',6'-dichlorosucrose, 6,6'-dichlorosucrose, 4,1',6'-trichlorosucrose, 4,6,6'-trichlorogalactosucrose, 4,1',5'-trichlorogalactosucrose-6-acetate, and 4,6,6'-trichlorogalactosucrose. Includes any organic or inorganic salt, carbohydrate, or acylated sucralose.

Solvent: as used herein includes a liquid that can dissolve another substance.

Sweetener product: as used herein includes any product comprising any combination or permutation of sucralose and/or any other sweeteners, including saccharin, aspartame, acesulfame potassium, cyclamate, alitame, stevioside, glucose, sucrose, fructose, levulose, maltose, lactose, any sugar alcohol, sorbitol, xylitol, and mannitol.

The present invention relates to novel methods for separating sucrose derivatives from impurities and includes methods of separating species of halogenated sucrose derivatives. Such methods enable one to separate, inter alia, sucralose from impurities and specifically other halogenated sugar impurities. The present invention also relates to novel extractive methods for purifying sucralose.

The present invention relates to improvements in efficiencies in separating sucralose from impurities. The invention relates to novel methods for the isolation and purification of compounds such as sucralose. The combination of an extraction in which the impurities more polar than sucralose are removed followed by an additional extraction that removes less polar impurities, for example, results in an effective purification process that provides a purified sucralose preparation.

The present invention includes, for example, a multiple step extractive process for removing impurities from a solution containing sucralose and impurities. The first extractive step comprises an extraction of a crude solution of sucralose in an aqueous or non-aqueous solvent with a second non-miscible solvent. In a specific embodiment, the ratio of the second solvent to the first solvent may be about 0.35:1, or from about 1:2 to about 1:5, or from about 1:3 to about 1:4 or, in another specific embodiment of the present invention, about 1:3.5. This extraction removes a substantial portion of the impurities that are less polar than sucralose. Optionally, the second solvent phase from this extraction can be washed with water, an aqueous solution, or a non-aqueous solvent to recover a portion of the sucralose that transferred to the second solvent phase. The crude sucralose solution remaining in the first solvent, optionally combined with the backwash of the second solvent, may then be subjected to a second extraction with a third solvent not miscible with the first solvent. This extraction may be carried out so as to transfer the bulk of the sucralose into the third solvent; hence, the impurities that are more polar than sucralose remain in the first solvent. The second and third solvents may be identical or they may be chemically distinct solvents. The partially purified sucralose may then recovered from the third solvent by crystallization or other separation procedures. Such procedures are readily available and known to those in the art. Indeed, one may specifically employ the crystallization methodologies as disclosed in U.S. Provisional Patent Application entitled "Process for Improving Sucralose Purity and Yield" filed on even date herewith and expressly incorporated by reference herein.

This combination of extractive steps relates to novel methods for substantially purifying sucralose without crystallization. The combination of an extraction in which the impurities less polar than sucralose are removed, followed by an additional extraction that removes more polar impurities, results in an effective purification process that provides a purified sucralose preparation. Furthermore, the judicious use of optimized ratios of solvents, extraction duration, and optimal extractive conditions allows the same solvent to be used to carry out the multiple extractive steps. Use of the same solvent in multiple steps decreases the inventory of solvents that must be maintained, and reduces safety and environmental concerns. As described in this application, ethyl acetate is a suitable exemplary solvent for these extraction steps.

Many extractive processes of this invention may employ as their feed mixtures compositions comprising sucralose and impurities, specifically impurities resulting from sucralose synthesis and, more specifically, related halogenated sucrose derivatives remaining from the synthetic process, residual ester intermediates, and/or organic and inorganic salts remaining from the synthetic process. These feed mixtures result from many synthetic processes for sucralose.

Solvents contemplated for use in the extractive steps include those that are immiscible with water or other solvents in which halogenated sucrose derivatives are readily soluble. Also included are solvents that are partially soluble in a first solvent such water, an aqueous solution, or other solvent in which halogenated sucrose derivatives are readily soluble, but in which the second solvent still forms a separate phase when mixed with the first solvent in proper ratios and under proper conditions. Solvents suitable for use within the embodiments of the present invention include, but are not limited to, n-pentane, n-hexane, Freon® TF, n-heptane, diethyl ether, 1,1,1 trichloroethane, n-dodecane, white spirit, turpentine, cyclohexane, amyl acetate, carbon tetrachloride, xylene, ethyl acetate, toluene, tetrahydrofuran, benzene, chloroform, trichloroethylene, Cellosolve® acetate, methyl ethyl ketone, acetone, diacetone alcohol, ethylene dichloride, methylene chloride, butyl Cellosolve®, pyridine, Cellosolve®, morpholine, dimethylformamide, n-propyl alcohol, ethyl alcohol, dimethyl sulphoxide, n-butyl alcohol, methyl alcohol, propylene glycol, ethylene glycol, glycerol, and water.

The choice of solvents may preferably be determined by the relative solubilities in the first and second solvents of sucralose and principal impurities resulting from the specific synthetic process employed. Additional factors germane to the choice of specific solvents include flammability, ease of recycling within the process, environmental concerns, toxicity, and cost. Solvents may be intentionally saturated with water or another solvent before use in the extraction steps. A wide range of both pure solvents and solvent combinations may be used to achieve the separations disclosed in this application, and therefore the scope of this invention is not intended to be limited to a specific solvent or combination of solvents.

The location and extent of halogenation, specifically chlorination, of a sucrose derivative strongly affects the polarity of the resulting compound. For example, various halogenated sucrose derivatives may be more polar or less polar than sucralose. More polar derivatives are more soluble in more polar solvents than sucralose. Likewise, less polar derivatives will be soluble in less polar solvents than sucralose. Therefore, the processes of the present invention make use of solvents, extraction temperatures and conditions, and solvent volume ratios that maximize the separation of sucralose and more or less polar impurities between solvent phases. One skilled in the art will readily recognize that a variety of solvent choices, extraction temperature and conditions, and solvent volume ratios can be used in the solvent extraction steps of the present invention to effect the desired separation of sucralose, for example, from various impurities, and specifically those impurities that are more or less polar than sucralose.

One aspect of the methods of the present invention relates to the selection of a first solvent and a second solvent. The second solvent, for example, is preferably sufficiently polar such that sucralose will at least partially partition from the first more polar solvent into the second less polar solvent, but the second solvent may preferably be sufficiently non-polar so that it remains immiscible with the first solvent. Examples of suitable more polar/less polar solvent pairs include water and ethyl acetate, water and methylisobutyl ketone, and water and methyltertiarybutyl ether. Although this invention is readily practiced with a binary solvent system (i.e., a system comprising two solvents), the use of ternary or even more complex solvent systems (i.e., systems comprising three or more solvents) is included within the scope of the present invention.

While the present invention is not bound by extant theories of solubility, standard international unit Hildebrand solubility parameters provide useful tools for assessing which solvent systems may function in the desired separations of the current invention. See generally John Burke, *Solubility Parameters: Theory and Application*, in 3 AIC BOOK AND PAPER GROUP INTERNATIONAL 13 (1984). The higher the solubility parameter associated with a solvent, the more polar that solvent. The solubility parameter for a mixture of miscible solvents is determined by the weighted average of the solubility parameter of the individual solvents in the mixture (weighted average of the individual solvents by volume). For example, amyl acetate (solubility parameter of 17.1) and methyl ethyl ketone (solubility parameter of 19.3) can be mixed in equal portions to yield a solvent mixture with the same solubility parameter as ethyl acetate (solubility parameter of 18.2). This mixture would have similar functionality to ethyl acetate in the separations that are part of the methods of the present invention.

Solvents that differ significantly in solubility parameter will not mix, but instead will be substantially immiscible. The different polarities of the solvents are also critical to the fractionation of dissolved material between the phases of an immiscible solvent system (this is typically a binary system of two phases, but of course ternary, quaternary, etc., systems can be advantageously used to separate complex mixtures).

More polar impurities in a solvent will partition into a solvent phase of a similar polarity and less polar impurities will partition into solvents of similar low polarity. Generally, the substitution of a chlorine group for a hydroxyl group renders a compound less polar (for example, the solubility parameter for methyl alcohol is 29.7, but the solubility parameter for methylene chloride is 20.2). Therefore, tetrachlorosucrose derivatives are less polar than sucralose, whereas di- and monochloro derivatives are relatively more polar.

Therefore, in the methods of the present invention, one skilled in the art using such known solvent polarities and solubilities can select a variety of solvents and solvent combinations to effect a separation of sucralose from impurities. For example, a difference in solubility parameter of about 20 units, and specifically of about 30 units, between or among solvent phases is contemplated in one aspect of the methods of the invention to produce the desired separations of sucralose and impurities. The Hildebrand parameter is empirical in nature, and based on chemical theory it can be divided into three component factors (dispersive force, polar force, and hydrogen bonding force).

Utilizing Hildebrand parameters as guides, one may endeavor to utilize, for example, three solvents in an extraction methodology: (a) one solvent with a high solubility parameter ("high solvent"), (b) one solvent with an intermediate solubility parameter ("intermediate solvent"), and (c) one solvent with a low solubility parameter ("low solvent").

For example, an extraction of an intermediate solvent containing sucralose and impurities with a low solvent will effect the transfer of impurities less polar than sucralose into the low solvent and provide an intermediate solvent with a higher ratio of sucralose to impurities less polar than sucralose. A second extraction of the intermediate solvent with the high solvent will effect the transfer of impurities more polar than sucralose into the high solvent and provide an intermediate solvent with a higher ratio of sucralose to impurities more polar than sucralose.

Similarly, an extraction of a low solvent containing sucralose and impurities with an intermediate solvent will effect the selective transfer of sucralose into the intermediate solvent and provide an intermediate solvent with a higher ratio of sucralose to impurities less polar than sucralose. A second extraction of the intermediate solvent with the high solvent will effect the transfer of impurities more polar than sucralose into said third solvent and provide an intermediate solvent with an increased ratio of sucralose to impurities more polar than sucralose.

The extraction steps used in aspects of the present invention may employ any of a number of available technologies for liquid-liquid extraction. These include methods of agitation in a standard vessel followed by settling and decanting, continuous column extractors, and/or continuous mixing and decanting. Batch, continuous and continuous countercurrent equipment can be used in the context of the present invention. Examples of this equipment include, but are not limited to, any Karr reciprocating plate column (Koch Inc., Kansas City, Mo.), any Scheibel Column (Koch Inc., Kansas City, Mo.), any packed column, any pulsed packed column, any bank of mixer-settlers, any bank of mixers and centrifugal separators, and any centrifugal counter current extractors (e.g., extractors manufactured by Robotel Inc., Pittsfield Mass.).

Indeed, a variety of extractive approaches may be advantageously employed in this invention, and the scope of the invention is therefore not intended to be limited to a specific configuration of equipment. Furthermore, the different process steps described herein (first extraction, backwash of the first extraction, and second extraction) may be performed in different vessels or pieces of equipment. Alternatively, all of these steps may be performed in the same vessel or, in certain aspects, in any order or simultaneously.

The sucralose preparations obtained by the methodologies of the present invention may be incorporated into a variety of products. Such products include, but are not limited to, beverages, combination sweeteners, consumer products, sweetener products, tablet cores (U.S. Pat. No. 6,277,409, which is expressly incorporated by reference herein), pharmaceutical compositions (U.S. Pat. Nos. 6,258,381; 5,817, 340; 5,593,696, which are expressly incorporated by reference herein), rapidly absorbed liquid compositions (U.S. Pat. No. 6,211,246, which is expressly incorporated by reference herein), stable foam compositions (U.S. Pat. No. 6,090,401, which is expressly incorporated by reference herein), dental floss (U.S. Pat. No. 6,080,481, which is expressly incorporated by reference herein), rapidly disintegrating pharmaceutical dosage forms (U.S. Pat. No. 5,876, 759, which is expressly incorporated by reference herein), beverage concentrates for medicinal purposes (U.S. Pat. No. 5,674,522, which is expressly incorporated by reference herein), aqueous pharmaceutical suspensions (U.S. Pat. Nos. 5,658,919; 5,621,005; 5,409,907; 5,374,659; 5,272,137, which are expressly incorporated by reference herein), fruit spreads (U.S. Pat. Nos. 5,397,588; 5,270,071, which are expressly incorporated by reference herein), liquid concentrate compositions (U.S. Pat. No. 5,384,311, which is expressly incorporated by reference herein), and stabilized sorbic acid solutions (U.S. Pat. No. 5,354,902, which is expressly incorporated by reference herein). The determination of an acceptable sweetness of products of the present invention may be accomplished by a variety of standard "taste test" protocols known in the art such as, for example, the protocols referred to in WO 00/01253 and Shamil & Birch, 25 Lebensm. Wiss. U. Technol. 192–96 (1992), which are expressly incorporated by reference herein.

The processes of this invention may be advantageously incorporated into more extensive processes for the purification of sucralose, where additional purification steps are employed before or after the extractions described herein. Further, steps to assay the materials of the extraction steps by HPLC or other methods in the art may be incorporated between the steps described herein. In addition, additional steps to purify or concentrate sucralose-containing solutions may be incorporated between the extraction steps described herein.

Vessel Based Extraction Method

Figure 1:
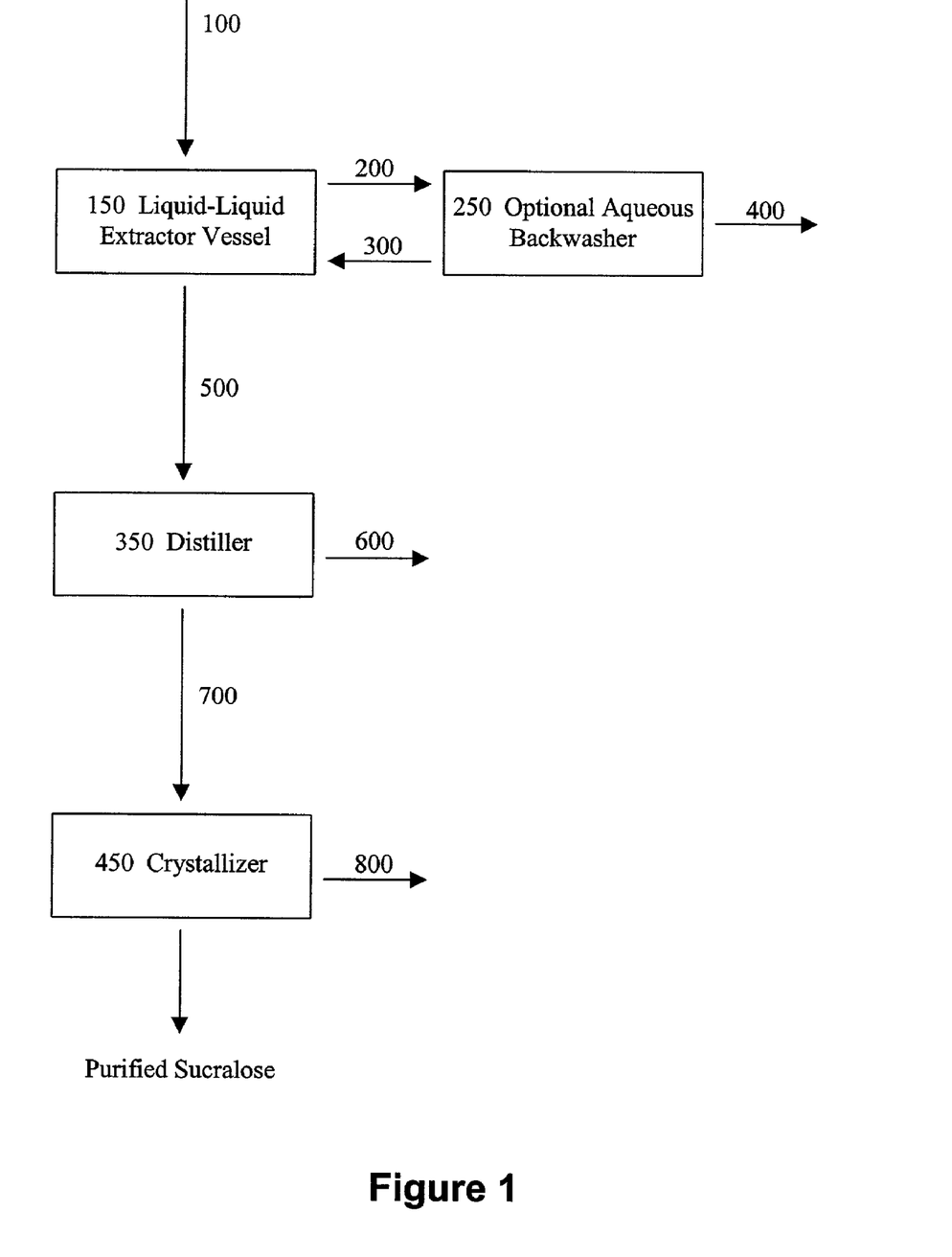
FIG. 1 provides a general schematic diagram of one embodiment of the methods of the present invention.

Referring to FIG. 1, one embodiment of a liquid-liquid extractive method of the present invention is shown. First, aqueous sucralose solution 100 may be fed into liquid-liquid extractor vessel 150, and may be extracted with a volume of ethyl acetate in a ratio of about 1:3.5 (ethyl acetate:aqueous solution). Impurities and a small portion of residual sucralose may be removed with the less polar ethyl acetate stream 200, while the majority of sucralose remains in the aqueous solution in liquid-liquid extractor vessel 150. Optionally, the ethyl acetate stream 200 may be backwashed with water in optional aqueous backwasher 250 to recover any residual sucralose from ethyl acetate stream 200. The less polar impurities may then be purged from the system with ethyl acetate solvent stream 400. Next, any remaining aqueous backwash 300 may be combined with the first aqueous solution in liquid-liquid extractor vessel 150. Sucralose may be extracted using ethyl acetate, for example, in a ratio of about 3:1 to about 4:1 ethyl acetate to water. The majority of sucralose will be transferred to the less polar ethyl acetate stream 500, and the more polar impurities remain in the aqueous phase. Ethyl acetate solvent stream 500 may then be fed to distiller 350 to remove residual water 600 present in the system. Purified sucralose in the ethyl acetate stream 700 may be fed to crystallizer 450 from which purified crystallized sucralose may be recovered, and any remaining impurities are removed with ethyl acetate solvent 800.

Column-Based Liquid Extraction Method

Figure 2:
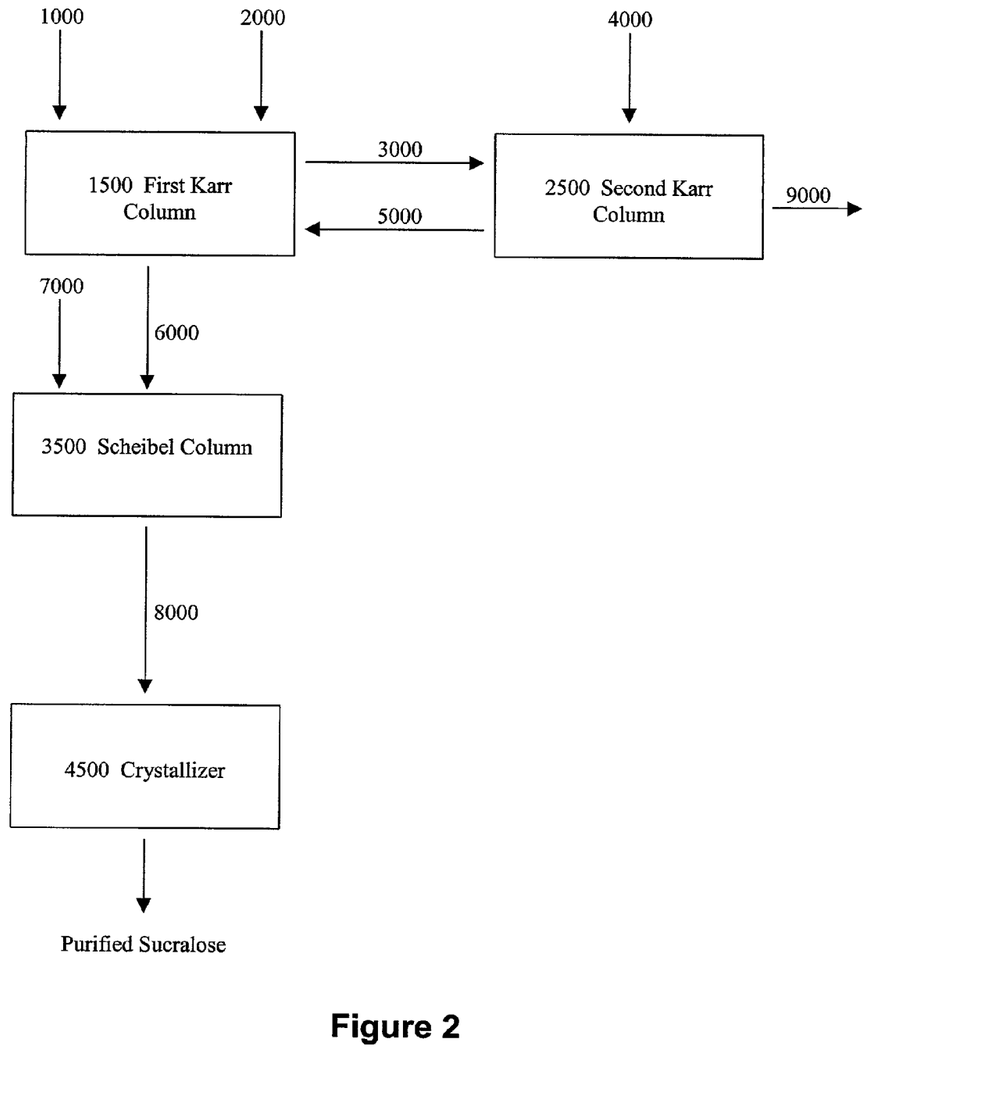
FIG. 2 provides a general schematic diagram of another embodiment of the methods of the present invention.

FIG. 2 depicts another embodiment of a liquid-liquid extractive method. First, the aqueous sucralose solution with impurities 1000 may be fed into the first Karr column 1500, where it may be combined with water-saturated ethyl acetate 2000 in a ratio of about 0.35:1 (ethyl acetate to water). Two distinct phases maybe obtained from the first Karr column 1500: the aqueous phase containing sucralose, and the ethyl acetate phase containing residual sucralose and impurities. The ethyl acetate stream 3000 may be introduced to the second Karr column 2500, where it may be combined with water 4000 in a ratio of about 0.7:1 (ethyl acetate to water) to recover the residual sucralose. Again, two distinct phases are formed in the second Karr column 2500: the aqueous phase containing recovered residual sucralose and an ethyl acetate phase. The aqueous stream 5000 from the second Karr column 2500 may be combined with the aqueous phase from the first Karr column 1500. The less polar impurities may then be purged from the system with ethyl acetate solvent stream 9000. The combined aqueous stream 6000 may be introduced into the Scheibel column 3500, and combined with ethyl acetate 7000 in a ratio of about 3:1 (ethyl acetate:water). The sucralose from the aqueous stream 6000 will be transferred to the less polar ethyl acetate 7000.

The purified sucralose in the ethyl acetate stream 8000 may be fed into the crystallizer 4500 from which purified sucralose may be recovered.

EXAMPLES

Without further elaboration, it is believed that one skilled in the art, using the preceding description, can utilize the present invention to the fullest extent. The following examples are illustrative only, and not limiting of the remainder of the disclosure in any way whatsoever.

Example 1

A sucralose solution containing various impurities can be obtained by a number of previously disclosed processes for synthesizing sucralose. See, e.g., U.S. Pat. No. 5,498,709. In an embodiment of the present invention, a 6-O-acyl sucralose derivative was deacylated and steam stripped to remove any dimethylformamide remaining from the chlorination reaction. This resulted in an aqueous solution containing sucralose, residual acylated sucralose, other halogenated sugar derivatives, and organic and inorganic salts.

This aqueous solution was introduced into a vessel suitable for liquid-liquid extraction, specifically, a 1inch diameter by 12 foot tall Karr reciprocating plate column (Koch, Inc., Kansas City, Mo.). The backwash was accomplished in a 2 inch diameter by 12 foot Karr column. There were 2 foot×6 inch diameter disengaging sections at the top and bottom of the columns.

The columns consisted of glass tubes with stainless steel plates with ⅜ inch holes supported from a central shaft. For the extraction, starting at the bottom of the column, the plates were spaced as follows: 1 foot at 6 inch spacing; 2 foot at 4 inch spacing; 1 foot at 3 inch spacing; 8 foot at 2 inch spacing. For the backwash, starting at the bottom of the column, the plates were spaced as follows: 2 foot at 4 inch spacing; 2 foot at 3 inch spacing; 7 foot at 2 inch spacing; 1 foot at 1 inch spacing.

Agitation was provided by lifting and lowering the plate stack using a connecting rod driven by an eccentric.

Positive displacement pumps were used to feed the extraction column and to empty the column bottoms. Water was supplied to the backwash column using a control valve and flow meter. The column overheads were allowed to overflow to intermediate tanks. Control was effected by varying the flow rates to maintain the interfaces in the middle of the column bottom disengaging sections. The upper interface was not controlled, but was checked from time to time for entrainment.

The aqueous solution was extracted with a volume of ethyl acetate in a ratio of 1:3.5 (ethyl acetate:aqueous solution). Although a portion of the sucralose was transferred into the ethyl acetate phase during this extraction, a proportionately greater amount of less polar impurities was removed with the ethyl acetate. Thus the majority of the sucralose remains in the aqueous solution. The ethyl acetate phase recovered from this first extraction is backwashed with water in a separate extraction step. This extraction removed a substantial portion of the sucralose, but not the impurities, from the ethyl acetate into the aqueous phase. The aqueous solution so obtained was then combined with the original feed and fed to the first extraction.

The following Table 1 provides the average amount of various impurities present in the ethyl acetate phase remaining after this extraction had been optimized. The conditions employed were: a) extraction: solvent to feed ratio=0.3 to 1 on a solute free basis; b) backwash: water to feed ratio=0.9 to 1 on a solute free basis; c) temperature: ambient in both extractions. The values are expressed as the ratio of the mass of impurity present to the mass of sucralose present in this phase. The impurities designated as unknowns are thought to be undefined chlorinated sucroses other than sucralose.

TABLE 1

| Impurity | Ratio to Sucralose |
| --- | --- |
| Unknown S 11.7 | 0.6 |
| Dichlorosucrose acetate | 0.7 |
| 6,1',6'-trichlorosucrose | 3.5 |
| 4,6,6'-trichlorosucrose | 1.2 |
| 4,1',4',6'-tetrachlorogalactotagatose | 3.5 |
| 4,1',6'-trichlorogalactosucrose-6-acetate | 0.4 |
| 4,6,1',6'-tetrachlorogalactosucrose | 10.6 |

The carbohydrate composition of the original sucralose solution was about 50–60% sucralose, with the balance comprising impurities such as those noted in the table above. Therefore, the ratio of sucralose to any individual impurity in this solution was greater than 1. Referring to Table 1, the less polar impurities (i.e., the tetrachloro-derivatives 4,1',4',6'-tetrachlorogalactotagatose and 4,6,1',6'-tetrachlorogalactosucrose) partition strongly into the ethyl acetate phase. Also, 6,1',6'-trichlorosucrose partitions into the less polar phase. Thus this initial extraction serves to remove a substantial portion of the less polar impurities from the sucralose solution.

The aqueous product stream from the extraction was then extracted with fresh ethyl acetate in a suitable vessel for liquid-liquid extraction, with the ratio of ethyl acetate to water in the range of 3:1 to 4:1. One suitable vessel for this extraction is a Karr reciprocating extraction column. This extraction served to transfer the majority of the sucralose into the ethyl acetate phase, and the more polar impurities as well as the inorganic salts remained in the aqueous phase. Table 2 provides the average amount of various impurities remaining in the aqueous solution after extraction. The values are expressed as the ratio of the mass of impurity present to the mass of sucralose present in this phase and reflect the averages of data obtained over multiple extractions.

TABLE 2

| Impurity | Ratio to Sucralose |
| --- | --- |
| 4,1'-dichlorogalactosucrose | 4.4 |
| 3',6'-dichloroanhydrosucrose | 5.2 |
| 4,6'-dichlorogalactosucrose | 32.0 |
| 1',6'-dichlorosucrose | 9.3 |
| Unknown G 5.7 | 0.4 |
| Unknown H 6.0 | 0.5 |
| 6,6'-dichlorosucrose | 0.9 |
| Unknown L 7.9 | 0.8 |
| 4,1',6'-trichlorosucrose | 0.5 |
| Unknown Q 10.5 | 0.8 |

The results in Table 2 show that sucralose is selectively removed to the ethyl acetate phase, leaving the aqueous phase with a much higher proportion of the more polar impurities. For example, various dichloro-derivatives, particularly 4,6'-dichlorogalactosucrose, constitute the bulk of the halogenated sucralose derivatives remaining in the aqueous phase. Thus this step achieves a substantial purification of sucralose away from the more polar impurities.

The ethyl acetate solution of sucralose and remaining impurities so obtained was then distilled to remove residual water present in the solution, and then sucralose was crystallized from the solution. Crystallization was facilitated by concentrating the solution as a result of evaporating a portion of the ethyl acetate, or by chilling the solution. Removal of water prior to crystallization greatly improved the rate of crystallization and the purity of the crystalline sucralose so obtained.

Example 2

An aqueous sucralose solution obtained by alkaline deacylation of a 6-O-acetyl precursor and subsequent neutralization was introduced into a Karr column with an internal diameter of 42 inches and an agitated height of 50 feet. Water-saturated ethyl acetate was introduced into the column at a ratio of 0.35:1 (0.35 parts of ethyl acetate to 1 part aqueous sucralose solution). Two phases were obtained from the column. The ethyl acetate phase was introduced into a Karr column with a 42 inch inside diameter and an agitated height of 58 feet. Water was also introduced into the column so that the ratio of water to the ethyl acetate phase was 0.7:1.0. The aqueous solution obtained from this backwash was combined with the original feed and fed to the first extraction. The aqueous phase from the first ethyl acetate extraction was introduced into a Scheibel column (Koch, Inc., Kansas City, Mo.) with an inside diameter of 56 inches, and agitated height of 33 feet. The column contained two 24 stage separation sections. Ethyl acetate was also introduced into the column in a ratio of 3:1 (ethyl acetate:water). The ethyl acetate phase was removed, and sucralose was recovered from the ethyl acetate phase by crystallization. Table 3 provides data on the impurities present in the ethyl acetate phase recovered from the first Karr column. Table 4 provides data on the impurities remaining in the aqueous phase after the extraction in the Scheibel column.

TABLE 3

| Impurity | Ratio to Sucralose |
| --- | --- |
| Unknown S | 0.14 |
| 6,1',6'-trichlorosucrose | 1.71 |
| 4,6,6'-trichlorogalactosucrose | 0.55 |
| 4,1',4',6'-tetrachlorogalactotagatose | 2.09 |
| 4,1',5'-trichlorogalactosucrose-6-acetate | 0.26 |
| 4,6,1'6'-tetrachlorogalactosucrose | 5.84 |

TABLE 4

| Impurity | Ratio to Sucrose |
| --- | --- |
| 4,1'-dichlorogalactosucrose | 1.79 |
| 3',6'-dichloroanhydrosucrose | 2.84 |
| 4,6'dichlorogalactosucrose | 13.90 |
| 1',6'-dichlorosucrose | 4.32 |
| Unknown G | 0.00 |
| Unknown H | 0.28 |
| 6,6'-dichlorosucrose | 0.40 |
| Unknown L | 0.47 |
| 4,1',6'-trichlorosucrose | 0.12 |
| Unknown Q | 0.04 |
| 4,6,6'-trichlorogalactosucrose | 0.02 |

Various modifications and variations of the described methods and systems of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are apparent to those skilled in the art are intended to be within the scope of the following claims.

What is claimed is:

1. A method for removing impurities from a starting composition including sucralose; first and second impurities, each of said first and second impurities comprising one or more related halogenated sucrose derivatives; and a first solvent; the method comprising the steps of:
   (a) extracting the starting composition with a second solvent at least partially immiscible with the first solvent to transfer the first impurities into said second solvent, thereby converting the starting composition to a partially purified composition comprising the sucralose, the second impurities, and the first solvent;
   (b) extracting the partially purified composition with a third solvent at least partially immiscible with the first solvent to transfer the sucralose into said third solvent while retaining the second impurities in said first solvent; and
   (c) recovering said sucralose from the third solvent via crystallizing said sucralose;
wherein the first impurities comprise tetrachlorosucrose, and wherein in step (a) at least half of the tetrachlorosucrose is transferred to the second solvent while at least half of the sucralose is retained in the first solvent.

2. A method for removing impurities from a starting composition including sucralose; first and second impurities, each of said first and second impurities comprising one or more related halogenated sucrose derivatives: and a first solvent; the method comprising the steps of:
   (a) extracting the starting composition with a second solvent, said second solvent, said second solvent at least partially immiscible with the first solvent and said second solvent including ethyl acetate, to transfer the first impurities into said second solvent, thereby converting the starting composition to a partially purified composition comprising the sucralose, the second impurities, and the first solvent; and
   (b) extracting the partially purified composition with a third solvent at least partially immiscible with the first solvent to transfer the sucralose into said third solvent while retaining the second impurities in said first solvent;
wherein the first impurities comprise tetrachlorosucrose, and wherein in step (a) at least half of the tetrachlorosucrose is transferred to the second solvent while at least half of the sucralose is retained In the first solvent.

3. A method for removing impurities from a starting composition including sucralose; first and second impurities, each of said first and second impurities comprising one or more related halogenated sucrose derivatives; and a first solvent; the method comprising the steps of:
   (a) extracting the starting composition with a second solvent at least partially immiscible with the first solvent to transfer the first impurities into said second solvent, thereby converting the starting composition to a partially purified composition comprising the sucralose, the second impurities, and the first solvent; and
   (b) extracting the partially purified composition with a third solvent, said third solvent at least partially immiscible with the first solvent and said third solvent including ethyl acetate, to transfer the sucralose into said third solvent while retaining the second impurities in said first solvent;
wherein the first impurities comprise tetrachlorosucrose, and wherein in step (a) at least half of the tetrachlorosucrose is transferred to the second solvent while at least half of the sucralose is retained in the first solvent.

4. A method for removing impurities from a starting composition including sucralose; first and second impurities, each of said first and second impurities comprising one or more related halogenated sucrose derivatives; and a first solvent; the method comprising the steps of:
   (a) extracting the starting composition with a second solvent at least partially immiscible with the first solvent to transfer the first impurities into said second solvent, thereby converting the starting composition to a partially purified composition comprising the sucralose, the second impurities, and the first solvent; and
   (b) extracting the partially purified composition with a third solvent at least partially immiscible with the first solvent to transfer the sucralose into said third solvent while retaining the second impurities in said first solvent, wherein the ratio of said second solvent to said first solvent is about 1:2 to about 1:5;
wherein the first impurities comprise tetrachlorosucrose, and wherein in stet, (a) at least half of the tetrachlorosucrose is transferred to the second solvent while at least half of the sucralose is retained in the first solvent.

5. The method of claim 4, wherein said ratio is about 1:3 to about 1:4.

6. A method for removing impurities from a starting composition including sucralose; first and second impurities, each of said first and second impurities comprising one or more related halogenated sucrose derivatives; and a first solvent; the method comprising the steps of:
   (a) extracting the composition with a second solvent at least partially immiscible with the first solvent to transfer the first impurities into said second solvent, thereby converting the starting composition to a partially purified composition comprising the sucralose, the second impurities, and the first solvent;
   (b) recovering said second solvent containing the transferred first impurities after extraction of said first solvent, backwashing said second solvent with a new portion of said first solvent, and combining at least part of said new portion with the partially purified composition; and
   (c) extracting the combined composition resulting from step (b) with a third solvent at least partially immiscible with the first solvent to transfer the sucralose into said third solvent white retaining the second impurities in said first solvent;
wherein the first impurities comprise tetrachlorosucrose, and wherein in step (a) at least half of the tetrachlorosucrose is transferred to the second solvent while at least half of the sucralose is retained in the first solvent.

7. A method for removing impurities from a starting composition comprising an aqueous solution of sucralose and first and second impurities, each of said first and second impurities comprising one or more related halogenated sucrose derivatives; the method comprising the steps of:
   (a) performing a first liquid extraction of said starting composition with an at least partially immiscible non-aromatic organic solvent to effect removal of the first impurities into said solvent, thereby converting the starting composition to a partially purified aqueous sucralose composition; and (b) performing a second liquid extraction of said partially purified aqueous sucralose composition with an organic solvent to effect the transfer of the sucralose into said organic solvent and the retention of the second impurities in the aqueous phase;

wherein the first impurities comprise tetrachlorosucrose, and wherein in step (a) at least half of the tetrachlorosucrose is transferred into the non-aromatic organic solvent while at least half of the sucralose is retained in the partially purified aqueous sucralose composition, and in step (b) at least half of the sucralose is transferred into the organic solvent of step (b).

8. The method of claim 7, further comprising the step of recovering said sucralose.

9. The method of claim 8, wherein said recovering step comprises crystallizing said sucralose.

10. The method of claim 7, wherein said solvent utilized in step (a) is ethyl acetate.

11. The method of claim 7, wherein said solvent utilized in step (b) is ethyl acetate.

12. The method of claim 7, wherein the ratios of said solvents to the aqueous phase are about 1:2 to about 1:5.

13. The method of claim 12, wherein said ratios are about 1:3 to about 1:4.

14. The method of claim 7, wherein said performing steps comprise a method of extraction selected from the group consisting of batch extraction, continuous extraction, and continuous countercurrent extraction.

15. A method for removing impurities from a starting composition comprising an aqueous solution of sucralose and first and second impurities, each of said first and second impurities comprising one or more related halogenated sucrose derivatives; the method comprising the steps of:
  (a) performing a first liquid extraction of said starting composition with an at least partially immiscible organic solvent to effect the transfer of the first impurities into said solvent, thereby converting the starting composition to a partially purified aqueous sucralose composition;
  (b) performing a second liquid extraction of said partially purified composition with an organic solvent to effect the transfer of the sucralose into said solvent and the retention of the second impurities in the aqueous phase;
  (c) extracting the organic solvent containing the transferred first impurities remaining from step (a) with an aqueous solution to effect the transfer of the sucralose present in the organic phase into the aqueous solution; and
  (d) combining the aqueous solution so obtained in step (c) with the aqueous solution recovered in step (a) prior to repeating step (b);

wherein the first impurities comprise tetrachlorosucrose, and wherein in step (a) at least half of the tetrachlorosucrose is transferred to the second solvent while at least half of the sucralose is retained In the partially purified aqueous sucralose composition.

16. The method of claim 15, wherein said step (b) effects the transfer of at least half of the sucralose into said solvent of step (b) and the retention of a portion of the impurities in the aqueous phase.

17. The method of claim 15, wherein said step (c) effects the transfer of a portion of the sucralose present In the organic phase into the aqueous solution.

18. The method of claim 15, further comprising the step of recovering said sucralose.

19. The method of claim 18, wherein said recovering step comprises crystallizing said sucralose.

20. The method of claim 15, wherein said solvent utilized in step (a) is ethyl acetate.

21. The method of claim 15, wherein said solvent utilized in step (b) is ethyl acetate.

22. The method of claim 15, wherein said each of steps (a), (b), and (c) independently comprises a method of extraction selected from the group consisting of batch extraction, continuous extraction, and continuous countercurrent extraction.

23. The method of claim 15, wherein step (c) comprises a method of extraction selected from the group consisting of batch extraction, continuous extraction, and continuous countercurrent extraction.

24. A method for removing tetrachlorosucrose compounds from a solution of sucralose and chlorinated sucrose derivatives in a first solvent comprising extracting the solution of sucralose and other chlorinated sucralose derivatives with an at least partially immiscible non-aromatic second solvent to effect the partition of the tetrachlorosucrose compounds into said second solvent and the retention of the sucralose in said first solvent, wherein said method effects the partition of at least half of the tetrachlorosucrose compounds into said second solvent and the retention of at least half of the sucralose in said first solvent.

25. The method of claim 24, wherein said tetrachlorosucrose compounds are selected from the group consisting of 4,1',4',6'-tetrachlorogalactotagatose and 4,6,1',6'-tetrachlorogalactosucrose.

26. The method of claim 24, wherein said extracting step comprises a method of extraction selected from the group consisting of batch extraction, continuous extraction, and continuous countercurrent extraction.

27. A method for removing impurities from a starting composition comprising a solution of sucralose and impurities comprising one or more related halogenated sucrose derivatives more polar than sucralose and one or more related halogenated sucrose derivatives less polar than sucralose in a first solvent; the method comprising the steps of:
  (a) performing a first liquid extraction of said starting composition with a second solvent that possesses a lower Hildebrand parameter than said first solvent under conditions that selectively transfer the impurities less polar than sucralose into said second solvent to provide a sucralose solution in said first solvent that has an increased ratio of sucralose to impurities less polar than sucralose, thereby converting the starting composition to a partially purified composition comprising sucralose, impurities more polar than sucralose, and the first solvent; and
  (b) performing a second liquid extraction of said partially purified composition with a third solvent that possesses a higher Hildebrand parameter than said first solvent under conditions that selectively transfer the impurities more polar than sucralose into said third solvent, thereby providing a sucralose solution in said first solvent with an increased ratio of sucralose to impurities more polar than sucralose;

wherein the impurities less polar than sucralose comprise tetrachlorosucrose; and wherein in step (a) at least half of the tetrachlorosucrose is transferred to the second solvent while at least half of the sucralose is retained in the first solvent.

28. The method of claim 27, further comprising the step of recovering said sucralose.

29. The method of claim 28, wherein said recovering step comprises crystallizing said sucralose.

30. The method of claim 27, wherein the ratio of said second solvent to said first solvent is about 1:2 to about 1:5.

31. The method of claim 30, wherein said ratio is about 1:3 to about 1:4.

32. The method of claim 27, wherein said performing steps comprise a method of extraction selected from the group consisting of batch extraction, continuous extraction, and continuous countercurrent extraction.

33. A method for removing impurities from a starting composition comprising a solution of sucralose and impurities comprising one or more related halogenated sucrose derivatives more polar than sucralose and one or more related halogenated sucrose derivatives less polar than sucralose in a first solvent, the method comprising the steps of:
(a) performing a first liquid extraction of said starting composition with a second solvent that possesses a higher Hildebrand parameter than said first solvent under conditions that selectively transfer at least half of the sucralose into said second solvent while retaining at least half of the impurities less polar than sucralose in the first solvent, thereby providing a sucralose solution in said second solvent that has an increased ratio of sucralose to the impurities less polar than sucralose; and
(b) performing a second liquid extraction of said sucralose solution in said second solvent obtained in the previous step with a third solvent that possesses a higher Hildebrand parameter than said second solvent under conditions that selectively transfer the impurities more polar than sucralose into said third solvent thereby providing a sucralose solution in said second solvent that has an increased ratio of sucralose to the impurities more polar than sucralose.

34. The method of claim 33, further comprising the step of recovering said sucralose.

35. The method of claim 34, wherein said recovering step comprises crystallizing said sucralose.

36. The method of claim 33, wherein the ratio of said second solvent to said first solvent is about 2:1 to about 5:1.

37. The method of claim 36, wherein said ratio is about 3:1 to about 4:1.

38. The method of claim 33, wherein said performing steps comprise a method of extraction selected from the group consisting of batch extraction, continuous extraction, and continuous countercurrent extraction.

* * * * *